(12) United States Patent
Quintero

(10) Patent No.: US 6,547,467 B2
(45) Date of Patent: Apr. 15, 2003

(54) MICROAPPLICATORS, DELIVERY SYSTEMS AND METHODS FOR ADHESIVES AND SEALANTS

(75) Inventor: Julian A. Quintero, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/941,217

(22) Filed: Aug. 29, 2001

(65) Prior Publication Data

US 2003/0044219 A1 Mar. 6, 2003

(51) Int. Cl.$^7$ .............................................. A61L 24/00
(52) U.S. Cl. ........................ 401/132; 206/438; 206/532; 206/813; 222/541.1; 401/133; 401/177; 401/179; 401/182; 401/183; 401/205; 401/219; 401/263; 401/270; 604/3; 604/232; 604/310; 604/311
(58) Field of Search ................................ 401/132, 133, 401/177, 179, 182, 183, 205, 219, 263, 270, 128; 222/541.1; 604/3, 232, 310, 311; 206/438, 532, 813

(56) References Cited

U.S. PATENT DOCUMENTS

| | | | |
|---|---|---|---|
| 2,721,858 A | 10/1955 | Joyner et al. .................. 260/67 |
| 3,254,111 A | 5/1966 | Hawkins et al. .......... 260/465.4 |
| 3,559,652 A | 2/1971 | Banitt et al. .................. 128/334 |
| 3,842,660 A | * 10/1974 | Van Buskirk ............... 73/61.54 |
| 3,940,362 A | 2/1976 | Overhults ................. 260/42.16 |
| 3,995,641 A | 12/1976 | Kronenthal et al. ......... 128/335 |
| 4,313,865 A | 2/1982 | Teramoto et al. ........... 260/31.4 |
| 4,364,876 A | 12/1982 | Kimura et al. ............ 260/465.4 |
| 4,560,723 A | 12/1985 | Millett et al. ................ 524/486 |
| 4,720,513 A | 1/1988 | Kameyama et al. ......... 523/203 |
| 5,130,369 A | 7/1992 | Hughes et al. ............... 524/846 |
| 5,216,096 A | 6/1993 | Hattori et al. ............... 526/201 |
| 5,328,687 A | 7/1994 | Leung et al. ............. 424/78.35 |
| 5,514,371 A | 5/1996 | Leung et al. ............. 424/78.35 |
| 5,514,372 A | 5/1996 | Leung et al. ............. 424/78.35 |
| 5,575,997 A | 11/1996 | Leung et al. ............. 424/78.35 |
| 5,582,834 A | 12/1996 | Leung et al. ................ 424/426 |
| 5,624,669 A | 4/1997 | Leung et al. ............. 424/78.35 |
| 5,888,005 A | * 3/1999 | Gueret .................... 401/130 X |
| 5,928,611 A | 7/1999 | Leung ......................... 422/131 |
| 5,989,205 A | 11/1999 | Pond et al. ...................... 604/3 |
| 6,143,352 A | 11/2000 | Clark et al. ................... 427/2.1 |
| 6,143,805 A | 11/2000 | Hickey et al. ............... 522/152 |
| 6,156,711 A | * 12/2000 | Perlman ...................... 510/118 |
| 6,183,593 B1 | 2/2001 | Narang et al. |

(List continued on next page.)

FOREIGN PATENT DOCUMENTS

GB  2 107 328 A  4/1983

OTHER PUBLICATIONS

U.S. patent application Ser. No. 09/834,615, Badejo et al., filed Apr. 2001.

(List continued on next page.)

Primary Examiner—Gregory Huson
Assistant Examiner—Kathleen Prunner
(74) Attorney, Agent, or Firm—Oliff & Berridge, PLC

(57) ABSTRACT

A microapplicator for dispensing and applying an adhesive or sealant material comprises a handle portion, an applicator tip connected to the handle portion, and a microreservoir at the applicator tip arranged to hold a small amount, about 20 microliters or less, of an adhesive/sealant material until dispensing. In embodiments, the applicator tip has a width of about 1 mm. The microapplicator may include a second reservoir, containing the adhesive/sealant material, that is arranged to supply the adhesive/sealant material to the microreservoir at the applicator tip. The second reservoir may comprise a frangible ampoule disposed in the handle portion, a container, such as a syringe, connected to the handle portion, or the handle portion itself. The applicator tip may comprise one of a polymer loop, a spatula, a rolling ball, a grate, a porous material, such as a swab, a foam pad or a mesh, and a brush.

68 Claims, 3 Drawing Sheets

U.S. PATENT DOCUMENTS

| | | | |
|---|---|---|---|
| 6,217,603 B1 | 4/2001 | Clark et al. | 606/214 |
| 6,238,120 B1 * | 5/2001 | Mark | 401/183 X |
| 6,238,212 B1 * | 5/2001 | Khachatoorian et al. | 433/89 |
| 6,310,166 B1 | 10/2001 | Hickey et al. | |
| 6,328,715 B1 * | 12/2001 | Dragan et al. | 604/232 |

OTHER PUBLICATIONS

U.S. patent application Ser. No. 09/630,437, Jonn et al., filed Aug. 2000.

U.S. patent application Ser. No. 09/919,877, Jonn et al., filed Aug. 2001.

U.S. patent application Ser. No. 09/430,289, D'Alessio et al., filed Oct. 1999.

U.S. patent application Ser. No. 09/430,177, Naran et al., filed Oct. 1999.

U.S. patent application Ser. No. 09/099,457, Malofsky et al., filed Jun. 1998.

U.S. patent application Ser. No. 09/430,180, Nicholson et al., filed Oct. 1999.

U.S. patent application Ser. No. 09/069,979, Narang et al., filed Apr. 1998.

U.S. patent application Ser. No. 09/430,176, Narang et al., filed Oct. 1999.

* cited by examiner

MICROAPPLICATORS, DELIVERY SYSTEMS AND METHODS FOR ADHESIVES AND SEALANTS

BACKGROUND OF THE INVENTION

This invention relates to microapplicators, delivery systems and methods for applying adhesive and sealant compositions such as cyanoacrylate adhesives, particularly for medical use.

Numerous swabs, applicators, dispensers and kits for dispensing and applying various materials, including adhesive materials, are known. However, these known arrangements possess various shortcomings that make them undesirable in many applications.

For example, U.S. Pat. No. 5,660,273 to Discko, Jr. discloses a package having wells or depressions for holding a medicament or material and an applicator for applying the medicament or material. The package includes a tray and a cover extending over the entire top surface of the tray. The tray includes an applicator well and a separate medicament well. A mixing area is placed on the cover. The tray further includes medicament wells and an applicator well. However, the '273 patent does not address providing effective storage and application of a polymerizable monomer compound. Moreover, the applicator disclosed in the '273 patent comprises a relatively large brush that is not suitable for certain medical applications.

U.S. Pat. No. 5,989,205 to Pond et al. discloses a solution applicator system having a retainer and a plurality of containers for holding a solution, such as fluoride or anesthetic, and an applicator member. Each container encloses the applicator and a solution-retaining receptacle with a puncturable sealing means. The '205 patent also does not address providing effective storage and application of a polymerizable monomer compound. Moreover, the applicator disclosed in the '205 patent comprises a relatively large swab that is not suitable for certain medical applications.

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and staples in wound closure as well as for covering and protecting tissue wounds such as lacerations, abrasions, burns, stomatitis, sores, and other open surface wounds. When such an adhesive is applied, it is usually applied in its monomeric form, and the resultant polymerization gives rise to the desired adhesive bond.

However, due to the need to apply the adhesive in its monomeric form, and due to the rapid polymerization rate of the monomers, applicators and/or delivery systems must counterbalance the competing requirements that the monomer not prematurely polymerize, that the monomer be easily applied, that the monomer polymerize at a desired rate upon application, and that the sanitary and/or sterile properties of the monomer and applicator—whether real or perceived— be maintained. This latter requirement, that the actual or perceived sanitary and sterile condition of the monomer and applicator be maintained, is particularly important in medical applications, where the user and/or the patient desires a clean product so as not to introduce further bacteria or foreign matter into a wound site. Further, applicators and/or delivery systems, as well as the monomer itself, should be sterilizable by conventional techniques.

In order to meet the above requirements, various packaging systems for monomeric adhesives have been proposed. These systems include large bottles with a single applicator, such as a large single- or multi-use brush; small applicators such as small ampoules containing monomer, for example within an internal frangible vial, that can be expelled through an integral applicator; and the like. However, a problem with many of these applicator systems is that the product contains more adhesive material than is necessary for a particular use. Because of the rapid polymerization rate of the monomers, any unused adhesive must often be discarded, because the remaining monomer undergoes polymerization, often within the applicator, to render the applicator unusable.

A further problem in addressing the above requirements of adhesive applicators and packaging is the need to provide a stable monomer product. Particularly in small quantities, cyanoacrylate monomers are prone to premature polymerization, which would render the product useless. Thus, industrial production of monomeric adhesive compositions has had to balance rapid cure rates and high bond strengths with shelf-life. The shelf-life of these adhesives is primarily related to stability (i.e., constancy of compositional nature), uncured physical properties, rate of cure of the adhesive, as well as final cured properties of the composition. For example, the shelf-life of a monomeric α-cyanoacrylate composition may be measured as a function of the amount of time the composition can be stored before unacceptable levels of polymerization, such as measured by viscosity increase, occur. Unacceptable levels are indicated by a level of polymerization product that reduces the usefulness of the composition in the application for which it is produced.

One proposed solution to this reduced shelf-life problem is to incorporate one or more stabilizers into the adhesive composition. For example, as disclosed in U.S. Pat. No. 3,559,652 to Banitt et al. and U.S. Pat. No. 5,582,834 to Leung et al., suitable stabilizers for medically useful α-cyanoacrylate compositions include Lewis acids such as sulfur dioxide, nitric oxide, and boron trifluoride, as well as free-radical stabilizers including hydroquinone, monomethyl ether hydroquinone, nitrohydroquinone, catechol, and monoethyl ether hydroquinone. The combination of the two anionic stabilizers sulfur dioxide and sulfonic acid is also known and is disclosed in, for example, British Patent Application GB 2 107 328 A.

However, while the proposed solution of adding stabilizers provides compositions that are more stable, a different problem arises. That new problem is that as the concentration of the added stabilizers increases in the composition, the cure rate of the composition tends to decrease. Thus, further components must be provided, such as in a separate composition, to be mixed with the adhesive composition (either directly or at the application site) to increase the polymerization rate of the monomer. Such additional materials, such as polymerization initiators or rate modifiers, increase the cost of the final composition, and may increase the complexity of use of the composition.

Known devices fail to provide applicators and delivery systems that are optimized for convenient dispensing and application of adhesive materials on a variety of surfaces and structures. The known applicators are generally either optimized for delivery of other compositions or are inconvenient or impractical for use in conjunction with adhesives or particular applications. Furthermore, such conventional devices and packaging generally do not address the competing needs of ease of use and adhesive stability prior to application.

SUMMARY OF THE INVENTION

The present invention addresses the above needs by providing microapplicators and delivery systems that permit economical and efficient use of adhesive and/or sealant compositions. In embodiments of the present invention, microapplicators and delivery systems are provided whereby a small amount, about 20 microliters or less, of the adhesive and/or sealant compositions may be dispensed and applied. In embodiments, the small amount preferably comprises about 15 microliters or less. In other embodiments, the small amount preferably comprises about 10 microliters or less. In still other embodiments, the small amount preferably comprises about 5 microliters or less.

Embodiments of the microapplicators and delivery systems of this invention are particularly suitable for medical applications. For example, embodiments of the microapplicators and delivery systems are suitable for bonding tissue for external medical applications including small incisions or lacerations, and for internal medical applications including anastomosis, such as vascular and duct anastomosis, and reconstruction and reattachment procedures, such as lymphatic, nerve and middle ear procedures.

In embodiments, the adhesive and/or sealant compositions comprise a polymerizable monomer compound. In such embodiments, the microapplicators and/or delivery systems may be formed entirely or partially of a material that provides stability and shelf-life to the adhesive/sealant composition. Accordingly, the need to apply separate polymerization initiators or rate modifiers can be reduced.

In embodiments, the microapplicators and delivery systems include a medicament for dispensing and applying with the adhesive/sealant material. In other embodiments, the microapplicators and delivery systems include a polymerization initiator or accelerator for the adhesive/sealant material.

In particular, the present invention is directed to a microapplicator for dispensing and applying an adhesive or sealant material, comprising: a handle portion; an applicator tip connected to the handle portion; and a microreservoir at the applicator tip arranged to hold a very small amount of an adhesive/sealant material until dispensing. In embodiments, the applicator tip comprises one of a polymer loop, a spatula, a rolling ball, a brush, a porous material, and the like. The porous material of the applicator tip may comprise one of a swab, a foam pad, a mesh, a grate comprising non-intersecting members, and the like. The tip of the applicator may comprise a plastic material or a material selected from the group consisting of metal, glass, paper, ceramics, cardboard, and the like. Further, the tip may comprise a polymerization initiator or accelerator for the adhesive/sealant material when the adhesive/sealant material comprises a polymerizable monomeric material. In such embodiments, an interior surface or any other suitable part of the tip may be coated and/or impregnated with the polymerization initiator or accelerator.

In various embodiments, the microapplicator includes a second reservoir containing the adhesive/sealant material. In such embodiments, the second reservoir is arranged to supply the adhesive/sealant material to the microreservoir at the applicator tip. According to various embodiments, the second reservoir may comprise a frangible ampoule disposed in the handle portion, a container connected to the handle portion, or the handle portion itself.

In embodiments, the container connected to the handle portion, or the handle portion itself, comprises a syringe having a barrel portion and a plunger portion that is movable in the barrel portion. The microapplicator may have a plug disposed between the adhesive/sealant material in the syringe and the microreservoir at the applicator tip that allows the adhesive/sealant material to pass during use. The plug may include a medicament. Additionally or alternatively, the plug may include a polymerization initiator or accelerator for the adhesive/sealant material when the adhesive/sealant material comprises a polymerizable monomeric material.

In various embodiments, the adhesive/sealant material comprises a polymerizable monomeric material. The polymerizable monomeric material may comprise, for example, a polymerizable 1,1-disubstituted ethylene monomer formulation or a cyanoacrylate formulation. In such embodiments, the second reservoir, the microreservoir and/or the applicator tip may be formed from a material that stabilizes the polymerizable monomeric material. In particular, the second reservoir, the microreservoir and/or the applicator tip may be formed from a halogenated polymeric material. The halogenated polymeric material may be selected from the group consisting of polyolefins, halogenated hydrocarbons, and engineered resins. In particular, the halogenated polymeric material may be a fluorinated polymeric material.

In other embodiments, the present invention is directed to a delivery system for an adhesive or sealant material, the delivery system comprising: a microapplicator having an applicator tip and a microreservoir at the applicator tip arranged to hold a very small amount of an adhesive/sealant material until dispensing, and a second reservoir containing the adhesive/sealant material. The secondary reservoir is connectable to the microapplicator to supply the adhesive/sealant material to the microreservoir at the applicator tip. In embodiments, the second reservoir comprises a sealed container that may be unsealed by connecting the sealed container to the microapplicator. In embodiments, the second reservoir comprises a handle when connected to the microapplicator. Various other embodiments of the delivery system according to this invention include the various features of the microapplicator discussed above and described further herein.

The present invention is also directed to methods of applying adhesive and sealant materials, especially to biological tissue. In embodiments, a microapplicator according to this invention is provided, a very small amount of an adhesive/sealant material is supplied to the microreservoir, and the adhesive/sealant is applied to a substrate to be bonded. In embodiments where the substrate to be bonded is tissue, the tissue may comprise a small incision or laceration. Further, in other embodiments, applying the adhesive/ sealant comprises anastomosis. In particular, applying the adhesive/sealant may comprise vascular anastomosis or duct anastomosis. In still other embodiments, applying the adhesive/sealant comprises reconstructing and/or reattaching tissue. In particular, applying the adhesive/sealant may comprise reconstructing and/or reattaching lymphatic, nerve and/or middle ear tissues.

In various embodiments, supplying the very small amount of an adhesive/sealant material to the microreservoir comprises moving a plunger toward the applicator tip. In other embodiments, supplying the very small amount of an adhesive/sealant material comprises breaking a frangible ampoule containing the adhesive/sealant material. In still other embodiments, supplying the very small amount of an adhesive/sealant material comprises squeezing the handle portion. In various embodiments, supplying the very small amount of an adhesive/sealant material comprises dipping the applicator tip into a secondary reservoir containing the adhesive/sealant material.

In other embodiments, a delivery system according to this invention is provided, the second reservoir is connected to the microapplicator, a very small amount of the adhesive/ sealant material is supplied to the microreservoir, and the adhesive/sealant is applied to a substrate to be bonded. In embodiments where the substrate to be bonded is tissue, the tissue may comprise a small incision or laceration. Further, in other embodiments, applying the adhesive/sealant comprises anastomosis. In particular, applying the adhesive/ sealant may comprise vascular anastomosis or duct anastomosis. In still other embodiments, applying the adhesive/ sealant comprises reconstructing and/or reattaching tissue. In particular, applying the adhesive/sealant may comprise reconstructing and/or reattaching lymphatic, nerve and/or middle ear tissues.

In various embodiments, supplying the very small amount of an adhesive/sealant material to the microreservoir comprises moving a plunger toward the applicator tip. In other embodiments, supplying the very small amount of an adhesive/sealant material comprises squeezing the second reservoir.

BRIEF DESCRIPTION OF THE DRAWINGS

Exemplary embodiments of the present invention are described in detail below, with reference to the attached drawing figures, in which.

DETAILED DESCRIPTION OF EXEMPLARY EMBODIMENTS

Figure 1:
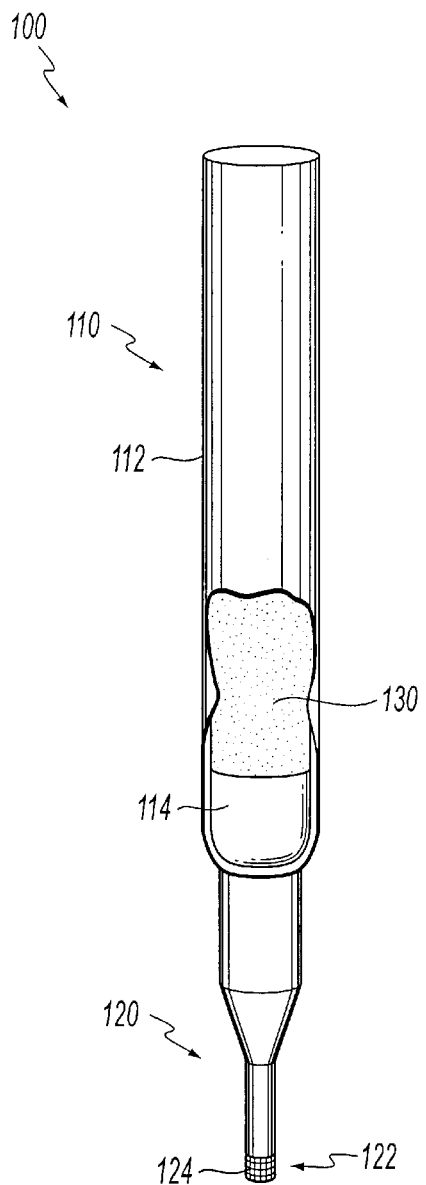
FIG. 1 is a side view of a microapplicator according to a first embodiment of the present invention.

FIG. 1 illustrates a first exemplary embodiment of the present invention, although the present invention is in no way limited to the specific design depicted therein. For the sake of description, the elements of the first embodiment, and subsequent embodiments, are illustrated as transparent. However, it should be understood that the elements need not be transparent in practice. Further, although particular dimensions of the applicator tip are described below, it should be understood that the size of the overall applicator is variable.

As shown in FIG. 1, a microapplicator 100 comprises a handle portion 110 and an applicator tip 120. The handle portion 110 may be formed as a hollow barrel 112 as shown. While the barrel 112 is shown as a cylindrical tube, other configurations are possible, such as a contoured outer surface to facilitate gripping and/or manipulation by hand. All components of the microapplicator 100 are preferably sterilizable by conventional techniques.

The applicator tip 120 comprises a microreservoir 122 that is designed to hold a very small amount of an adhesive or sealant material until dispensing. The very small amount is on the order of 20 microliters or less, preferably about 15 microliters or less, more preferably about 10 microliters or less, and most preferably about 5 microliters or less. The applicator tip 120 and the microreservoir 122 are designed for delivering very small amounts, such as about 3 microliters or less, of an adhesive or sealant material. This is unattainable using known applicator tips or delivery methods because such applicator tips and delivery methods generally rely on the formation of droplets, which have a size much greater than 3 microliters.

More particularly, the applicator tip 120 and the microreservoir 122 are designed so that the surface tension of the adhesive or sealant material retains about 20 microliters or less in the microreservoir 122 until delivery. For certain configurations and materials, amounts greater than 20 microliters may be difficult to retain using the surface tension of some adhesive or sealant materials. Since the amount of adhesive or sealant material is held in the microreservoir 122 by surface tension, a controlled delivery of 1–3 microliters is possible.

As shown in FIG. 1, the applicator tip 120 may comprise a mesh 124 that facilitates controlled application of the adhesive/sealant material dispensed from the microreservoir 122. In various embodiments of this invention, the applicator tip 120 may comprise a polymer loop, a spatula, a rolling ball, a brush, a grate or another porous material, such as a fibrous swab or a foam pad, or the like, rather than the mesh 124 shown in the first embodiment. Any suitable applicator tip can be used that allows for application of the adhesive/ sealant material to a desired site, and thus different applicator tips may be appropriate for different application methods.

The applicator tip can have a variety of suitable shapes, including, but not limited to, conical, cylindrical, chisel, planar (flat), or polygonal shapes such as rectangular or trapezoidal. The length and size of the tip can be varied depending on various application parameters. For certain applications, the tip is preferably about 1 millimeter in width. The tip may be detachable from the applicator body, or may be an integral part of the applicator.

The applicator tip 120 can be composed of any of a variety of materials including polymerized materials such as plastics, foams, rubber, thermosets, films, membranes, or the like. Additionally, the applicator tip 120 may be composed of materials such as metal, glass, paper, ceramics, cardboard, and the like. The applicator tip 120 material may be porous, absorbent, or adsorbent in nature to enhance and facilitate application of the adhesive/sealant material. In general, the only limitation on the materials used to fabricate the tip is that the tip must be sufficiently compatible with the adhesive/sealant material that undesirable effects on the adhesive/sealant material do not prevail during contact of the adhesive/sealant material with the applicator tip 120.

The handle portion 110 may comprise a second reservoir containing an adhesive or sealant material 130. In such a case, the barrel 112 is preferably sealed at least at an end remote from the applicator tip 120. Prior to use, the applicator tip 120 is also preferably sealed to prevent contamination of the microapplicator 100 or the adhesive/sealant material 130. Further, the barrel 112 may be flexible so that the barrel 112 can be squeezed to supply a very small amount of the adhesive/sealant material 130 to the microreservoir 122. The very small amount of the adhesive/sealant material 130 may also be supplied to the microreservoir 122 gravitationally or by any other suitable means.

The amount of the adhesive/sealant material 130 in the barrel 112, for example, may be sufficient to perform a specific procedure for a single patient. In other words, an amount suitable for a single use may be provided in the barrel 112. Since any desired amount of the adhesive/sealant material 130 may be provided in the barrel 112, the barrel 112 may include markings that indicate a volume or "dosage" contained therein.

Alternatively, a second reservoir (not shown) containing the adhesive/sealant material 130 may be provided separately from the microapplicator 100. In such a case, the applicator tip 120 may be dipped into the second reservoir to fill the microreservoir 120 with a desired amount of the adhesive/sealant material 130. This may be accomplished with or without using a plunger, such as that shown in FIG. 2, movably fitted in the barrel 112.

The adhesive/sealant material 130 may comprise a polymerizable monomeric material. More specifically, in various embodiments, the polymerizable monomeric material may comprise a polymerizable 1,1-disubstituted ethylene monomer formulation, such as a cyanoacrylate formulation. When the adhesive/sealant material 130 comprises a polymerizable monomeric material, the barrel 112 is preferably sealed to avoid premature polymerization of the monomer. As noted above, the end remote from the applicator tip 120 may be sealed, for example, by a fixed barrier or a removable plug or cap. The barrel 112 may be completely sealed by a seal at the applicator tip 120 or by a pierceable or frangible barrier (not shown) disposed between the adhesive/sealant material 130 and the applicator tip 120.

Additionally, when the adhesive/sealant material 130 comprises a polymerizable monomeric material, the applicator tip 120 may comprise a polymerization initiator or accelerator for the adhesive/sealant material 130. For example, a polymerization initiator or accelerator may be coated on an inside surface of the applicator tip 120. Although not limited to any particular initiators or placement thereof, suitable initiators are disclosed in, for example, U.S. patent application Ser. No. 09/834,615 filed Apr. 16, 2001, Ser. No. 09/630,437 filed Aug. 2, 2000, and Ser. No. 09/919,877 filed Aug. 2, 2001, the entire disclosures of which are incorporated herein by reference.

Also, when the adhesive/sealant material 130 comprises a polymerizable monomeric material, the barrel 112 comprising the second reservoir may be formed of a material that stabilizes the polymerizable monomeric material, preferably even in the absence of stabilizers being added to the polymerizable monomeric material. Other elements of the microapplicator 100, such as the microreservoir 122 and/or the applicator tip 120, or the entire applicator, may be formed of the same or similar materials that stabilize the polymerizable monomeric material. Thus, it is possible and preferred in embodiments of the present invention that the adhesive composition does not include, or is substantially free of, one or more stabilizer components such as are known and used in the art as additives to the adhesive monomer composition. This may reduce, or even eliminate, the need for a polymerization initiator or accelerator.

For example, the barrel 112 may be formed of, or coated by, a halogenated polymeric material, such as, but not limited to, polyolefins, halogenated hydrocarbons (halocarbons) and engineered resins. The ability of such halogenated polymers to provide barrier properties, and contribute to stability of adhesive compositions, is described in further detail in copending U.S. application Ser. No. 09/430,289, filed Oct. 29, 1999, the entire disclosure of which is incorporated herein by reference. Likewise, in embodiments, the materials can include functionalized polymeric materials, such as are disclosed in the '289 application, where the functionalization provides the desired stabilizing effect to the adhesive/sealant material 130. Of course, in embodiments, it may be desirable and/or necessary to add a separate stabilizer component to the adhesive composition, either to completely stabilize or fine-tune the stabilization characteristics of the adhesive/sealant material 130.

Where polymer materials are used to form elements of the microapplicator 100, the elements may comprise a halogenated, preferably fluorinated, polymer on at least an internal surface thereof, at least in the area in contact with the adhesive/sealant material 130. As used herein, a "halogenated polymer" can be any halogenated polymer that is known or becomes known in the art or can be any polymeric material that is suitable for fabrication of elements that are subsequently or concurrently halogenated by at least one known halogenation method. However, the halogenation process must not render the polymeric material unusable for the microapplicator 100. As used herein, a "fluorinated polymer" is thus a halogenated polymer, wherein the halogen comprises, in whole or in part, fluorine.

The stabilizing material preferably comprises any suitable halogenated polymeric material, including, but not limited to, polyolefins, halogenated hydrocarbons (halocarbons), and engineered resins. The packaging, including any of the parts of the microapplicator, can comprise homopolymers, copolymers, higher order polymers, or mixtures thereof, and can comprise one species of polymeric material or mixtures of multiple species of polymeric material. As desired and/or necessary, the polymeric materials can be halogenated or otherwise functionalized either prior to manufacture of the microapplicator 100, during manufacture of the microapplicator 100, or subsequent to manufacture of the microapplicator 100. Pre-halogenated (or pre-functionalized) materials are generally those that are already halogenated or functionalized, such as where halogenated or functionalized monomers are used to form the elements of the microapplicator 100. Concurrently halogenated or functionalized materials are those where although the precursor materials may not themselves be halogenated or functionalized, the halogenation or functionalization is introduced during the manufacturing process. For example, where the elements of the microapplicator 100 are made by molding, the halogenation or functionalization can be introduced by using a reactive halogen-containing gas. Likewise, post-halogenated or post-functionalized materials are those where the microapplicator 100 is first prepared, and then the formed polymeric material is subsequently halogenated or functionalized.

Stabilizing materials of the present invention can, for example, comprise polyolefin polymers. Suitable polyolefins include, but are not limited to, polyethylene (PE), such as high-density polyethylene (HDPE), medium-density polyethylene (MDPE); low-density polyethylene (LDPE), cross-linked high-density polyethylene (XLPE), linear low-density polyethylene (LLDPE), ultra low-density polyethylene, and very low-density polyethylene; polycarbonate (PC); polypropylene (PP); polypropylene copolymer (PPCO); polyallomer (PA); polymethylpentene (PMP or TPX); polyketone (PK); polyethylene terephthalates (PET), including polyethylene terephthalate G copolymer (PETG) and oriented PET; polystyrene (PS); polyvinylchloride (PVC); naphthalate; polybutylene terephthalate; thermoplastic elastomer (TPE); mixtures thereof; and the like. Exemplary densities of the above polyethylenes are as follows: LDPE—0.910–0.925 $g/cm^3$; medium-density polyethylene (MDPE)—0.926–0.940 $g/cm^3$; HDPE—0.941–0.965 $g/cm^3$. Other densities can be determined by the ordinary artisan by referencing, for example, ASTM D 1248 (1989).

The elements of the microapplicator of the present invention can comprise halogenated hydrocarbons (also referred to herein as halocarbons). For example, exemplary fluorinated hydrocarbons include, but are not limited to, Halar® ethylene-chlorotrifluoroethylene copolymer (ECTFE) (Allied Chemical Co., Morristown, N.J.); Tefzel® ethylene-tetrafluoroethylene (ETFE) (duPont, Wilmington, Del.); tetrafluoroethylene (TFE); polytetrafluoroethylene (PTFE); fluorinated ethylene propylene (FEP); polytetrafluoroethylene fluorinated ethylene propylene (PTFE-FEP); polyvinyl fluoride (PVF); polytetrafluoroethylene perfluoroalkoxy (PTFE-PFA); polyvinylidene fluoride (PVDF); mixtures thereof; and the like.

The elements of the microapplicator of the present invention can comprise engineered resins. Exemplary engineered resins include, but are not limited to, polyamide, such as nylon; polyphenylene oxides (PPO); polysulfone (PSF); mixtures thereof; and the like.

In embodiments, the elements of the microapplicator of the present invention can comprise mixtures of the above polyolefins, halogenated hydrocarbons, and/or engineered resins.

As shown in FIG. 1, the microapplicator 100 may include a plug 114 that is situated between the adhesive/sealant material 130 in the barrel 112 and the microreservoir 122 at the applicator tip 120. The plug 114 may be porous or may include one or more passageways (not shown) so that the plug 114 allows the adhesive/sealant material 130 to pass during use. For example, if the plug 114 is porous, the pressure generated by squeezing the barrel 112 causes the adhesive/sealant material 130 to pass during use. If the plug 114 includes a passageway, then a rupturable membrane (not shown) may be used to block flow of the adhesive/sealant material 130 prior to use.

The plug 114 may be used to regulate or limit the flow of the adhesive/sealant material 130 so that only the desired small amount is supplied to the microreservoir 122. Different flow characteristics may be achieved by adjusting the porosity of the plug 114 or the size of and/or number of passageways in the plug 114.

The plug 114 may include a medicament, either therein or thereon, that is supplied to the microreservoir 122 along with the very small amount of the adhesive/sealant material 130 for dispensing and application. Additionally or alternatively, the plug may comprise a polymerization initiator or accelerator for the adhesive/sealant material 130 when the adhesive/sealant material 130 comprises a polymerizable monomeric material. In such a case, a rupturable membrane (not shown) may be used to separate the polymerization initiator or accelerator from the adhesive/sealant material 130 prior to use.

Figure 2:
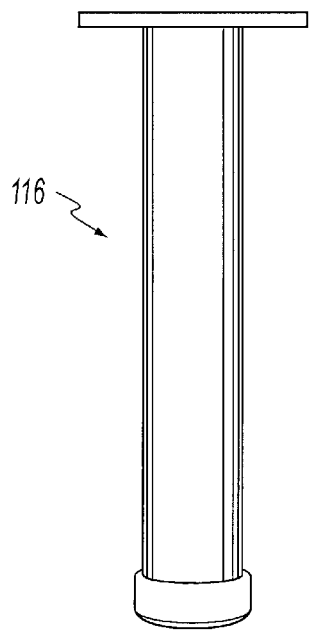
FIG. 2 is a side view of a plunger corresponding to a first modification of the embodiment of FIG. 1.

In a modification of the first embodiment, the microapplicator 100 may include a plunger 116, as shown in FIG. 2, that is movable within the barrel 112. The plunger 116 may be placed in the barrel 112 after the barrel 112 is filled with a desired amount of the adhesive/sealant material 130. During use, the plunger 116 is moved in the barrel 112 towards the applicator tip 120 so that a very small amount of the adhesive/sealant material 130 is supplied to the microreservoir 122. When the plug 114 is included, the pressure on the adhesive/sealant material 130 generated by the movement of the plunger 116 forces the adhesive/sealant material 130 through the plug 114 and the rupturable membrane, if provided.

Figure 3:
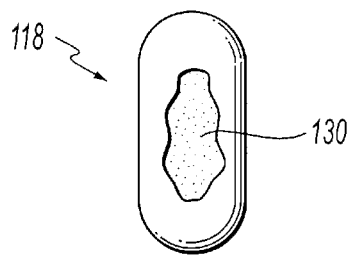
FIG. 3 is a side view of an ampoule corresponding to a second modification of the embodiment of FIG. 1.

In another modification of the first embodiment, the microapplicator 100 may include a frangible ampoule 118, as shown in FIG. 3, that contains the adhesive/sealant material 130. Thus, according to this modification, the frangible ampoule 118 comprises the second reservoir. The frangible ampoule 118 may be placed in the barrel 112 of the microapplicator 100 just prior to, or well before use. During use, in any known or hereafter developed manner, the frangible ampoule 118 is broken to release the adhesive/sealant material 130. For example, the barrel 112 may be flexible so that the frangible ampoule 118 may be compressed and broken by squeezing the barrel 112. As noted above, squeezing the barrel 112 may also be used to supply the adhesive/sealant material 130 to the microreservoir 122.

The frangible ampoule 118 may be maintained separate from the microapplicator 100 prior to use. In such a case, the frangible ampoule 118 and the microapplicator 100 comprise a delivery system according to this invention. An end of the barrel 112 remote from the applicator tip 120 arranged to be openable/closable so that the frangible ampoule 118 can be inserted into the barrel 112. For example, the end of the barrel 112 remote from the applicator tip 120 may include a removable or openable cap (not shown). Once inserted, the frangible ampoule 118 may be broken as described above.

The delivery system offers advantages and flexibility since multiple frangible ampoules 118 may be used with a single microapplicator 100. For example, the frangible ampoule 118 may be selected based on the amount of the adhesive/sealant material 130 contained therein. Alternatively, a standardized amount may be contained in each frangible ampoule 118, allowing a user to use as many or as few of the frangible ampoules 118 as needed for a given application. Further, frangible ampoules 118 containing different adhesive/sealant materials 130 may be selected for use with the microapplicator 100.

Figures 4, 5:
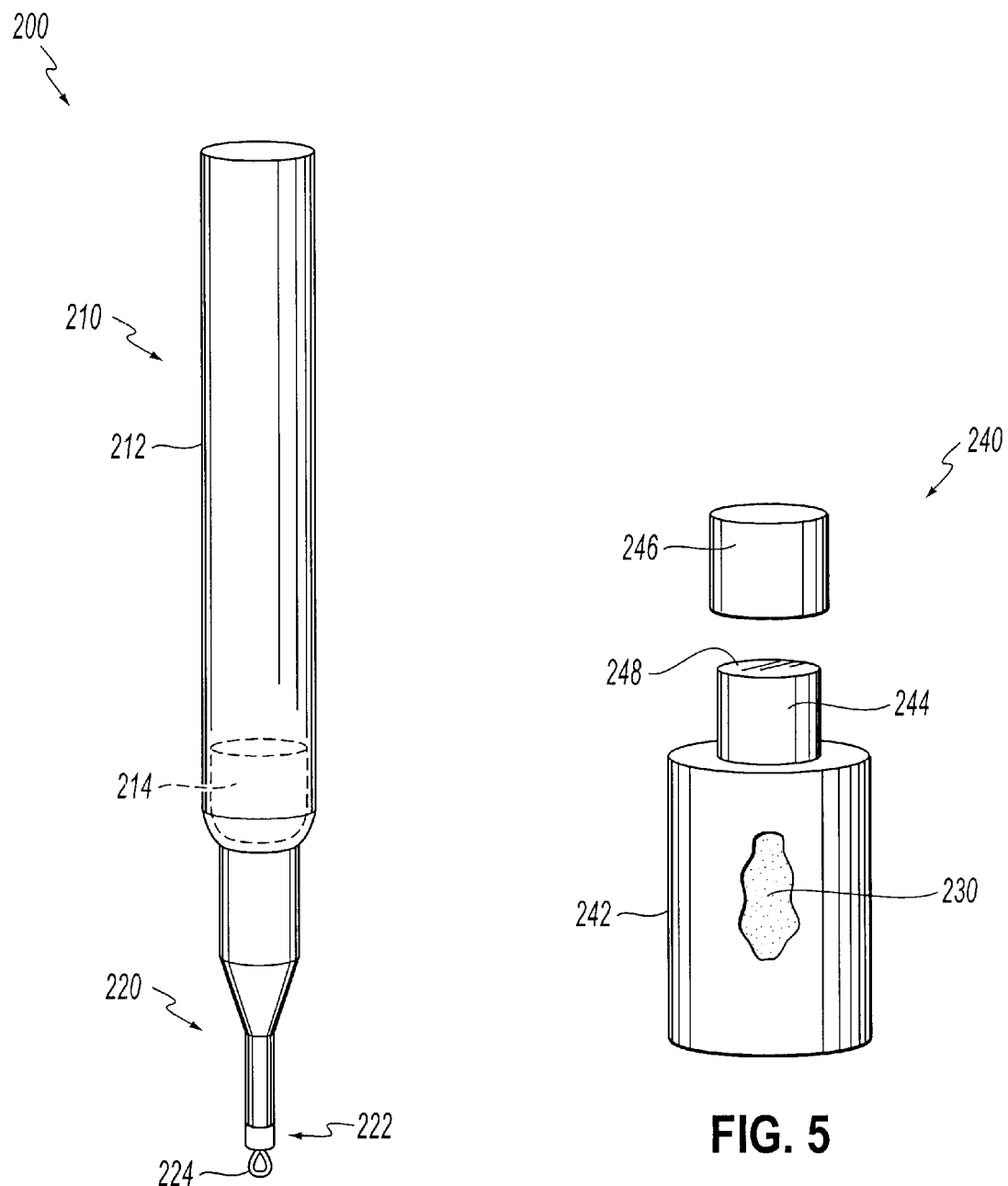
FIG. 4 is a side view of a microapplicator portion of a delivery system according to a second embodiment of the present invention.
FIG. 5 is a side view of a second reservoir portion of the delivery system according to the second embodiment.

FIGS. 4 and 5 illustrate a second exemplary embodiment of the present invention. As shown in FIG. 4, a microapplicator 200 comprises a handle portion 210 and an applicator tip 220. The handle portion 210 may be formed as a hollow barrel 212 as shown. The applicator tip 220 comprises a microreservoir 222 that is designed to hold a very small amount of an adhesive or sealant material until dispensing. As shown in FIG. 4, the microreservoir 222 may comprise a polymer loop 224 that facilitates controlled application of the adhesive/sealant material dispensed from the microreservoir 222. The polymer loop 224 may comprise a curvedloop shape, as shown, or may be a squared-loop shape or any other shape that is suitable for a given application.

As described above, the applicator tip 220, the microreservoir 222 and the polymer loop 224 are designed so that the surface tension of the adhesive or sealant material retains the very small amount of an adhesive or sealant material until dispensing. It has been found that the polymer loop 224 is ideal for applying 2–3 microliters of an adhesive or sealant material. The amount of adhesive or sealant material held in the microreservoir 222 may be adjusted, for example, by changing the size of the polymer loop 224.

The microapplicator 200 together with a container 240, shown in FIG. 5, comprise a delivery system according to this invention. The container 240 comprises a second reservoir 242 containing an adhesive or sealant material 230. The container 240 is preferably sealed. For example, a neck 244 of the container 240 may cooperate with a cap 246 that seals the container 240. Alternatively, or additionally, a seal 248 such as a membrane may be provided over an opening in the neck 244.

The container 240 is connectable to the microapplicator 200 to supply the adhesive/sealant material 230 to the microapplicator 200. For example, the neck 244 of the container 240 may be designed to engage an open end of the handle portion 210. The connection between the container 240 and the microapplicator 200 may be of any suitable configuration, such as a snap-fit, a friction-fit, a screw-fit, a locking connection, or the like. Preferably, the connection is at least substantially sealing to avoid leakage and/or contamination of the adhesive/sealant material 230.

The container 240 and/or a portion of the microapplicator 200 may be flexible so that the very small amount of the adhesive/sealant material 230 can be supplied to the microreservoir 222, as described above. The very small amount of the adhesive/sealant material 230 may also be supplied to the microreservoir 222 gravitationally or by any other suitable means. As shown, the microapplicator 200 may also include a plug 214, as described above with respect to the first exemplary embodiment.

The second exemplary embodiment of a delivery system according to this invention offers advantages and flexibility as described above. Multiple containers 240 may be used with a single microapplicator 200 so that an amount or kind of the adhesive/sealant material 230 can be selected for a given application.

Figure 6:
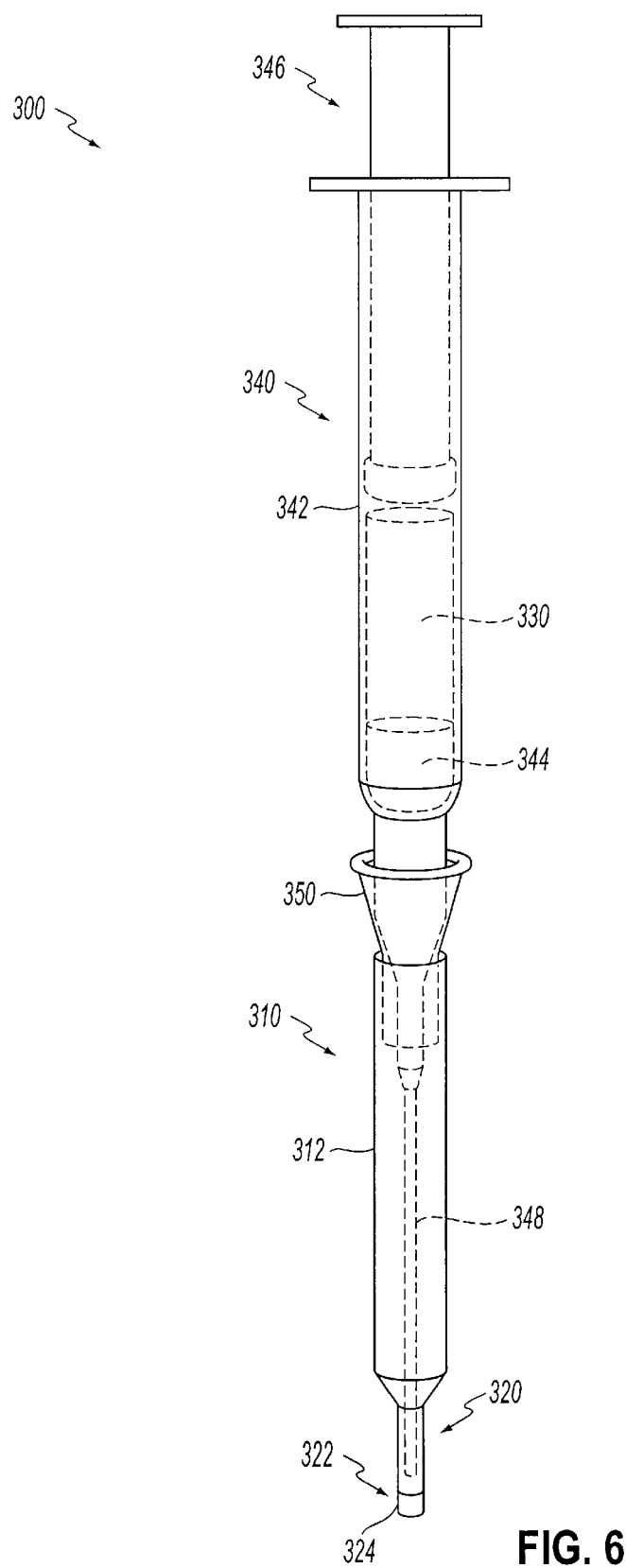
FIG. 6 is a side view of a delivery system according to a third embodiment of the present invention.

FIG. 6 illustrates a third exemplary embodiment of the present invention. As shown in FIG. 6, a microapplicator 300 comprises a handle portion 310 and an applicator tip 320. The handle portion 310 may be formed as a hollow barrel 312 as shown. The applicator tip 320 includes a microreservoir 322 that is designed to hold a very small amount of an adhesive or sealant material until dispensing. As shown in FIG. 6, the applicator tip 320 may comprise a spatula 324 that facilitates controlled application of the adhesive/sealant material dispensed from the microreservoir 322.

The microapplicator 300 together with a syringe 340 and a funnel connector 350 comprise a delivery system according to this invention. The syringe 340 comprises a second reservoir containing an adhesive or sealant material 330. The syringe 340 includes a barrel portion 342 and a plunger portion 346. The syringe 340 may also include a plug 344, as described above. Also, the syringe 340 may include a dispensing needle 348 that may extend into the applicator tip 320 adjacent to the microreservoir 322.

As shown, the funnel connector 350 may be used to facilitate a connection between the microapplicator 300 and the syringe 340. However, the connection between the syringe 340 and the microapplicator 300 may be of any suitable configuration, including, but not limited to, a snap-fit, a friction-fit, a screw-fit, a locking connection, or the like. Preferably, the connection is at least substantially sealing to avoid leakage and/or contamination of the adhesive/sealant material 330.

The delivery system according to the third exemplary embodiment operates similarly to the first modification of the first embodiment described above.

The microapplicators and delivery systems of the present invention may be used to apply the polymerizable adhesive composition to a variety of substrates for the purposes of protecting, sealing, and/or bonding surfaces together. Suitable substrates include, but are not limited to, metals, plastics, rubbers, wood, ceramics, fabrics, cement, paper, living tissue and the like. For example, the polymerizable and/or cross-linkable material may be useful as tissue adhesives, sealants for preventing bleeding or for covering open wounds, systems for delivery of therapeutic or other bioactive agents, and other biomedical applications. They find uses in, for example, closing surgically incised or traumatically lacerated tissues; setting fractured bone structures; retarding blood flow from wounds; aiding repair and regrowth of living tissues; providing implantable matrixes for delivering bioactive agents; dressing burns; dressing skin or other superficial or surface wounds (such as abrasions, chaffed or raw skin, and/or stomatitis); protecting tissues prone to damage (e.g., as artificial calluses); and providing structural implants.

The monomer (including prepolymeric) adhesive composition may include one or more polymerizable monomers. Preferred monomers that may be used in this invention are readily polymerizable, e.g. anionically polymerizable or free radical polymerizable, or polymerizable by zwitterions or ion pairs to form polymers. Such monomers include those that form polymers, that may or may not biodegrade. Such monomers are disclosed in, for example, U.S. Pat. Nos. 5,328,687 and 5,928,611 to Leung et al., U.S. patent application Ser. No. 09/430,177, filed on Oct. 29, 1999, and U.S. patent application Ser. No. 09/471,392 filed Dec. 23, 1999, which are hereby incorporated in their entirety by reference herein. Preferred monomers include 1,1-disubstituted ethylene monomers, such as α-cyanoacrylates including, but not limited to, alkyl α-cyanoacrylates having an alkyl chain length of from about 1 to about 20 carbon atoms or more, preferably from about 2 to about 12 or more preferably from about 3 to about 8 carbon atoms. Mixtures of two or more monomers may also be used, if desired.

The α-cyanoacrylates of the present invention can be prepared according to several methods known in the art. U.S. Pat. Nos. 2,721,858, 3,254,111, 3,995,641, and 4,364,876, each of which is hereby incorporated in its entirety by reference herein, disclose methods for preparing α-cyanoacrylates.

In other embodiments, the monomeric material can include such polymerizable monomeric materials as alkyl ester cyanoacrylates and alkyl ether cyanoacrylates. Such cyanoacrylates are disclosed in, for example, U.S. patent applications Ser. No. 09/630,437 filed Aug. 2, 2000, and Ser. No. 09/919,877 filed Aug. 2, 2001, the entire disclosures of which are incorporated herein by reference. Suitable blends of one or more monomers, as disclosed in the latter-referenced application, may also be used, as desired.

As desired, the application according to the present invention can include any of a wide variety of additional materials, either mixed into the polymerizable composition, or in a separate compartment from the polymerizable composition. Examples of suitable additional materials include, but are not limited to, plasticizing agents, thixotropic agents, thickeners, natural or synthetic rubbers, stabilizers, pH modifiers, bioactive agents, cross-linking agents, chain transfer agents, fibrous reinforcements, colorants, preservatives, formaldehyde reducing or scavenging agents, flavorants, perfumes, mixtures thereof, and the like.

The composition may optionally also include at least one other plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to tributyl citrate, acetyl tri-n-butyl citrate (ATBC), polymethylmethacrylate, polydimethylsiloxane, hexadimethylsilazane, isopropyl myristate, isopropyl palmitate, and others as listed in U.S. patent application Ser. No. 09/471,392 filed Dec. 23, 1999, the disclosure of which is incorporated in its entirety by reference herein.

The composition may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. No. 4,720,513, and U.S. patent application Ser. No. 09/374,207 filed Aug. 12, 1999, the disclosures of which are hereby incorporated in their entireties by reference herein.

The composition may optionally also include thickeners. Suitable thickeners may include poly (2-ethylhexy methacrylate), poly(2-ethylhexyl acrylate) and others as listed in U.S. patent application Ser. No. 09/471,392 filed Dec. 23, 1999, and Ser. No. 09/374,207, filed Aug. 12, 1999, the disclosures of which are incorporated by reference herein in their entirety.

The composition may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313, 865 and 4,560,723, the disclosures of which are hereby incorporated in their entireties by reference herein.

The composition may optionally also include one or more stabilizers, preferably both at least one anionic vapor phase stabilizer and at least one anionic liquid phase stabilizer. The composition may optionally also include, in addition to or in place of the anionic stabilizers, at least one free radical stabilizer. These stabilizing agents may inhibit premature polymerization. Suitable anionic and free radical stabilizers may include those listed in U.S. patent application Ser. No. 09/471,392 filed on Dec. 23, 1999, and Ser. No. 09/099,457, filed Jun. 18, 1998, the disclosures of which are incorporated by reference herein in their entirety.

However, as described above, a particular advantage of the present invention, such as in embodiments where stabilizing packaging is used, is that separate stabilizers can be omitted form the composition. Thus, in embodiments, the polymerizable composition preferably does not include any, or at least substantially none, additional stabilizer.

The compositions may also include pH modifiers to control the rate of degradation of the resulting polymer, as disclosed in U.S. Pat. No. 6,143,352, the entire disclosure of which is hereby incorporated by reference herein in its entirety.

Compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites, etc. Additional examples of formaldehyde scavenger compounds useful in this invention and methods for their implementation can be found in U.S. Pat. Nos. 5,328,687, 5,514,371, 5,514,372, 5,575,997, 5,582,834 and 5,624,669, all to Leung et al., which are hereby incorporated herein by reference in their entireties.

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated herein in its entirety by reference, discloses exemplary cross-linking agents.

The compositions of this invention may further contain fibrous reinforcement and colorants such as dyes, pigments, and pigment dyes. Examples of suitable fibrous reinforcement include PGA microfibrils, collagen microfibrils, and others as described in U.S. patent application Ser. No. 09/471,392 filed on Dec. 23, 1999, the disclosure of which is incorporated by reference herein in its entirety.

The polymerizable compositions useful in the present invention may also further contain one or more preservatives, for prolonging the storage life of the composition. Suitable preservatives, and methods for selecting them and incorporating them into adhesive compositions, are disclosed in U.S. patent application Ser. No. 09/430,180, the entire disclosure of which is incorporated herein by reference.

In embodiments of the present invention, the composition and/or its applicator or dispenser may contain additional materials such as a polymerization initiator, accelerator, rate-modifier, and/or cross-linking agent for initiating polymerization and/or cross-linking of the polymerizable monomer material. Such initiators, accelerators, rate-modifiers, and/or cross-linking agents can be included in the applicator tip, in the polymerizable composition, and/or elsewhere, as appropriate. This is advantageous, for example, where additional initiator or accelerator may be necessary to provide the desired cure rate of the adhesive once it is applied or where additional treatment is desired. Furthermore, this is advantageous in embodiments where additional stabilizers or polymerization inhibitors must be added to the adhesive composition in the assembly, so as to overcome the "cure speed loss" that often occurs when such stabilizing agents are added.

In embodiments, the initiator or accelerator material is an initiator and/or a rate modifier for polymerization and/or cross-linking of a polymerizable monomer. As used herein, a polymerization initiator is any material that causes a monomer composition applied to a substantially dry tissue (i.e., substantially in the absence of plasma or like tissue fluids) to polymerize in less than 300 seconds at ambient temperature, for example, at approximately 21–25° C. Preferably, the initiator causes the monomer composition to polymerize in less than 150 seconds at ambient temperature, more preferably within 60, 90 or 130 seconds. As used herein, a polymerization rate modifier is any material that changes the rate at which a polymerizable monomer would polymerize in the absence of that material. Preferably, the rate modifier accelerates the rate of the polymerization reaction, although for particularly fast-acting monomers it may decelerate that rate.

The material may be applied to the applicator tip, for example, by spraying, dipping, injecting, or brushing the applicator tip with a liquid medium containing the polymerization initiator or accelerator. It is preferably applied to the tip by dipping or injecting. For example, it may be applied to the tip by pumping of the liquid medium, for example, through a syringe, onto the tip. Methods of applying the polymerization initiator or accelerator to an applicator tip are described in more detail in U.S. Pat. Nos. 5,928,611 and 6,217,603 to Leung and U.S. patent application Ser. No. 09/069,979, filed Apr. 30, 1998, and Ser. No. 09/430,177, filed Oct. 29, 1999, the entire disclosures of which is incorporated herein by reference.

As described above, an advantage of the present invention is that the applicators and dispensers can be provided in various single-use sizes, based on the desired or intended uses of the adhesive compositions. In such embodiments, the applicator tip size and/or the amount of polymerizable adhesive composition can be selected from various alternatives. This concept further applies to the amount of polymerization initiator or accelerator that can be added. For example, in embodiments where polymerization initiator or accelerator is added to the applicator tip, the amount can be adjusted based on the desired or intended uses of the adhesive compositions. Thus, for example, where an application would require only a small amount of adhesive composition, a correspondingly small amount of initiator or accelerator can be applied to an appropriately sized applicator tip; likewise, where an application would require a larger amount of adhesive composition, a correspondingly larger amount of initiator or accelerator can be applied to an appropriately larger applicator tip.

Particular initiators and accelerators for particular monomers may be readily selected by one of ordinary skill in the art without undue experimentation. Control of the molecular weight distribution of the applied adhesive can be enhanced by selection of the concentration and functionality of the initiator or accelerator vis-a-vis the selected monomer. Suitable polymerization initiators and accelerators for cyanoacrylate compositions include, but are not limited to, detergent compositions; surfactants, including nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

In preferred embodiments, the initiator may be a bioactive material, including quaternary ammonium halides such as domiphen bromide and alkylbenzyldimethylammonium chloride (benzalkonium chloride; BAC) their pure components, or mixtures thereof, especially those with an alkyl containing 6–18 carbon atoms; benzethonium chloride; and salts of sulfadiazine. Cobalt napthenate can be used as an accelerator for peroxide. As used herein, a "bioactive" material is one that provides beneficial effects, such as wound healing effects, in addition to serving its primary function as, for example, an initiator. Other suitable bioactive materials are disclosed in U.S. Pat. Nos. 5,928,611 and 6,217,603 to Leung and U.S. patent application Ser. No. 09/430,176 filed Oct. 29, 1999, and Ser. No. 09/430,177, filed Oct. 29, 1999, the entire disclosures of which is incorporated herein by reference.

The polymerizable adhesive compositions according to the invention can also comprise a medicament. Inclusion of a medicament is often desirable in compositions intended for medical applications. The medicament can either be added to the monomer-containing adhesive composition prior to packaging, or, alternatively, to the applicator tip or a separate compartment. Thus, the medicament may be applied to a tissue prior to or simultaneously with application of the monomer-containing adhesive composition. In addition to serving its medicinal function, the medicament may be selected so that it functions in conjunction with the co-packaged polymerizable monomer composition to initiate polymerization of the monomer or modify (e.g., accelerate) the rate of polymerization for the monomer to form a polymeric adhesive. The proper combination of medicament and polymerizable monomer can be determined easily by one of skill in the art. The medicament is supplied in an amount that will be pharmaceutically effective when applied topically (i.e., directly to tissue).

Examples of such medicaments include, but are not limited to antibiotics, antimicrobials, antiseptics, bacteriocins, bacteriostats, disinfectants, steroids, anesthetics, fungicides, anti-inflammatory agents, antibacterial agents, antiviral agents, antitumor agents, growth promoters, and mixtures thereof.

Exemplary medicaments include, but are not limited to, quaternary ammonium halides such as benzalkonium chloride and benzethonium chloride; chlorhexidine sulfate; gentamicin sulfate; hydrogen peroxide; quinolone thioureas; silver salts, including, but not limited to, silver acetate, silver benzoate, silver carbonate, silver chloride, silver citrate, silver iodide, silver nitrate, and silver sulfate; sodium hypochlorite; salts of sulfadiazine, including, but not limited to silver, sodium, and zinc salts; and mixtures thereof.

Preferable medicaments are those that are anions or help in radical generation or that are ion pairs or are themselves radicals.

In embodiments, the medicament is preferably a quaternary ammonium halide such as alkylbenzyldimethylammonium chloride (benzalkonium chloride; BAC) with an alkyl containing 6–18 carbon atoms, its pure components, or mixtures thereof, or benzethonium chloride; or a salt of sulfadiazine, such as a silver, sodium, or zinc salt.

The medicament can have a pharmaceutical effect only at the site of application (i.e., limited to the tissue on/in which it is applied), or it can have a systemic effect (by systemic, it is not only meant that the medicament has an effect throughout the patient's body, but also at a specific site other than the site of application). In embodiments where the medicament is applied in an amount sufficient to show a systemic pharmaceutical activity, it can be absorbed, transported, or otherwise distributed to the site or sites within the patient where the pharmaceutical activity is desired, e.g., through the cardiovascular or lymph systems. The medicament may be in the form of a solid, such as a powder or a solid film, or in the form of a liquid, such as a watery, viscous, or paste-like material. The medicament may also be compounded with a variety of additives, such as surfactants or emulsifiers, and vehicles.

The polymerizable and/or cross-linkable material may be neat (no additional compounds added) or in a solvent, emulsion or suspension. Suitable solvents according to the present invention include alcohol, ether alcohol, hydrocarbons, halogenated hydrocarbons, ethers, acetals, ketones, esters, acids, sulfur- or nitrogen-containing organic compounds, mixtures thereof and the like. Other suitable solvents are disclosed in U.S. Pat. No. 5,130,369 to Hughes et al. and U.S. Pat. No. 5,216,096 to Hattori et al., the entire disclosures of which are incorporated herein by reference. These solvents may be used either independently or in combination of two or more. They may also be used in conjunction with water to the extent that the polymerizable and/or cross-linkable material is dissolved or suspended in such a mixture. The total amount of solvent that may be incorporated into the polymerizable and/or cross-linkable material may be 0 to 99, preferably 1 to 50, and more preferably 3 to 25 percent by weight. Selection of the amount will, of course, depend on the desired monomer and process conditions, and amounts outside these ranges may be acceptable.

In embodiments, the monomer composition and/or its packaging are preferably sterilized. Sterilization of the monomer composition and/or its packaging can be accomplished by techniques known to one of ordinary skill in the art, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation, as described in U.S. Pat. No. 6,143,805, the entire disclosure of which is incorporated herein by reference. Further sterilization methods for the composition include sterile filtration (aseptic) techniques. The composition must show low levels of toxicity to living tissue during its useful life. In preferred embodiments of the present invention, the composition is sterilized to provide a Sterility Assurance Level (SAL) of at least $10^{-3}$. In embodiments, the Sterility Assurance Level may be at least $10^{-4}$, or may be at least $10^{-5}$, or may be at least $10^{-6}$.

The polymerizable adhesive composition according to the invention can be manufactured and sterilized in very small quantities. Typically, sterilized α-cyanoacrylate compositions are sterilized in large volumes (e.g., 1–5 milliliters). When intended for medical applications, this large volume is undesirable because much of the composition is discarded after the first use out of fear of contamination of the composition. Thus, providing sterile α-cyanoacrylate compositions in smaller volumes is desirable. Thus, the sterilized compositions of embodiments of the invention provide an improvement over the sterile compositions currently available.

Preferably, a polymerizable adhesive composition according to the invention is packaged such that a total volume of no more than 1 mL of the adhesive composition is present per package (i.e., container). More preferably, no more than 0.6 ml. Or no more than 0.2 ml of the adhesive composition is present. As noted above, such compositions of the invention can be sterilized by appropriate means, including, but not limited to, dry heat sterilization, gamma irradiation, microwave irradiation, and electron beam irradiation.

In embodiments where the compositions are to be used for medical applications, the composition is preferably sterilized. For example, sterilized compositions according to embodiments of the present invention show an increase in viscosity of no more than 300% as a result of sterilization. Viscosity levels can be determined by known techniques. For example, viscosity can be determined at room temperature (approximately 21–25° C.) using a Brookfield Cone-Plate Viscometer with spindle size CP-40. The instrument is standardized using a Viscosity Reference Standard in the same range as the sample to be tested.

To be considered sterile, the polymerizable adhesive composition should show no bacterial growth after inoculation onto Soybean Casein Digest media, and incubation for 14 days at 32–35° C. Standard procedures and materials, such as those disclosed in USP XXIII<1211>, "Sterilization and Sterility Assurance of Compendial Articles" should be followed.

Preferably, the polymerizable adhesive composition has, immediately after sterilization, a viscosity level no more than 15–20% higher than the level prior to sterilization. However, the acceptable viscosity can be as high as 200% higher than the level prior to sterilization. More preferably, the sterilized composition has a viscosity that is no more than 50% higher than the viscosity of the composition before sterilization. Most preferably, the composition has a viscosity that is essentially unchanged from the level prior to sterilization (i.e., less than 20% higher). In general, the increase in viscosity during sterilization can be viewed as "premature" aging of the monomer-containing composition, which reduces its useful shelf life, particularly when it is not stored at reduced temperature. In addition, the change in the viscosity is also an indication of a change in the reactivity of the monomeric composition, which normally is not desired.

In preferred embodiments, there is substantially no initiation of polymerization of monomeric liquid adhesive compositions that affects the utility of the monomer or monomers caused by the sterilization process. The sterilized liquid adhesive compositions have a good shelf life and excellent stability.

It should be understood that the individual features of the various exemplary embodiments may be included or excluded as desired for a given application. As such, all possible combinations of the described features are considered to be encompassed by the present invention.

Thus, while the present invention has been described in terms of exemplary embodiments, it is to be understood that the present invention is not to be limited to the particular configuration of these embodiments. One skilled in the art will recognize that various modifications and/or alterations of these embodiments may be made while remaining within the scope of the present invention.

What is claimed is:

1. A microapplicator for dispensing and applying an adhesive or sealant material, comprising:
   a handle portion;
   an applicator tip connected to the handle portion; a reservoir containing the adhesive/sealant material and being formed in the hand portion; and a microreservoir formed in the applicator tip and being in fluid communication with the reservoir, the microreservoir being configured to hold only about 20 microliters or less of the adhesive/sealant material until dispensing.

2. The microapplicator of claim 1,
the reservoir is arranged to supply the adhesive/sealant material to the microreservoir at the applicator tip.

3. The microapplicator of claim 2, wherein the adhesive/sealant material comprises a polymerizable monomeric material.

4. The microapplicator of claim 3, wherein the polymerizable monomeric material comprises a polymerizable 1,1-disubstituted ethylene monomer.

5. The microapplicator of claim 3, wherein the polymerizable monomeric material comprises a cyanoacrylate.

6. The microapplicator of claim 3, wherein at least the second reservoir is formed from a material that stabilizes the polymerizable monomeric material.

7. The microapplicator of claim 6, wherein at least the second reservoir is formed from a halogenated polymeric material.

8. The microapplicator of claim 7, wherein the halogenated polymeric material is selected from the group consisting of polyolefins, halogenated hydrocarbons, and engineered resins.

9. The microapplicator of claim 7, wherein the halogenated polymeric material is a fluorinated polymeric material.

10. The microapplicator of claim 6, wherein the second reservoir, the microreservoir and the applicator tip are formed from a material that stabilizes the polymerizable monomeric material.

11. The microapplicator of claim 6, wherein the second reservoir, the microreservoir and the applicator tip are formed from a halogenated polymeric material.

12. The microapplicator of claim 11, wherein the halogenated polymeric material is selected from the group consisting of polyolefins, halogenated hydrocarbons, and engineered resins.

13. The microapplicator of claim 11, wherein the halogenated polymeric material is a fluorinated polymeric material.

14. The microapplicator of claim 2, wherein the second reservoir comprises a frangible ampoule disposed in the handle portion.

15. The microapplicator of claim 2, wherein the second reservoir comprises a container connected to the handle portion to supply the adhesive/sealant material to the microreservoir at the applicator tip.

16. The microapplicator of claim 15, wherein the container comprises a syringe having a barrel portion and a plunger portion that is movable in the barrel portion.

17. The microapplicator of claim 16, further comprising a plug including a medicament, the plug being disposed between the adhesive/sealant material in the syringe and the microreservoir at the applicator tip, the plug allowing the adhesive/sealant material to pass during use.

18. The microapplicator of claim 16, further comprising a plug including a polymerization initiator or accelerator for the adhesive/sealant material, the plug being disposed between the adhesive/sealant material in the syringe and the microreservoir at the applicator tip, the plug allowing the adhesive/sealant material to pass during use, wherein the adhesive/sealant material comprises a polymerizable monomeric material.

19. The microapplicator of claim 2, wherein the handle portion comprises the second reservoir.

20. The microapplicator of claim 19, wherein the handle portion comprises a syringe having a barrel portion and a plunger that is movable in the barrel portion.

21. The microapplicator of claim 20, further comprising a plug including a medicament, the plug being disposed between the adhesive/sealant material in the syringe and the microreservoir at the applicator tip, the plug allowing the adhesive/sealant material to pass during use.

22. The microapplicator of claim 20, further comprising a plug including a polymerization initiator or accelerator for the adhesive/sealant material, the plug being disposed between the adhesive/sealant material in the syringe and the microreservoir at the applicator tip, the plug allowing the adhesive/sealant material to pass during use, wherein the adhesive/sealant material comprises a polymerizable monomeric material.

23. The microapplicator of claim 2, further comprising a plug including a medicament, the plug being disposed between the adhesive/sealant material in the second reservoir and the microreservoir at the applicator tip, the plug allowing the adhesive/sealant material to pass during use.

24. The microapplicator of claim 2, further comprising a plug including a polymerization initiator or accelerator for the adhesive/sealant material, the plug being disposed between the adhesive/sealant material in the second reservoir and the microreservoir at the applicator tip, the plug allowing the adhesive/sealant material to pass during use, wherein the adhesive/sealant material comprises a polymerizable monomeric material.

25. The microapplicator of claim 1, wherein the applicator tip comprises a porous material.

26. The microapplicator of claim 25, wherein the porous material of the applicator tip comprises one of a swab, a foam pad and a mesh.

27. The microapplicator of claim 1, wherein the applicator tip comprises a brush.

28. The microapplicator of claim 1, wherein the applicator tip comprises a spatula.

29. The microapplicator of claim 1, wherein the applicator tip comprises a rolling ball.

30. The microapplicator of claim 1, wherein the applicator tip comprises a dropper.

31. The microapplicator of claim 1, wherein the applicator tip comprises a polymer loop.

32. The microapplicator of claim 1, wherein the applicator tip comprises a material selected from the group consisting of metal, glass, paper, ceramics and cardboard.

33. The microapplicator of claim 1, wherein the tip of the applicator comprises a plastic material.

34. The microapplicator of claim 1, wherein the adhesive/sealant material is sterilized.

35. The microapplicator of claim 34, wherein at least the microreservoir and the applicator tip are sterilized.

36. The microapplicator of claim 1, wherein the small amount of the adhesive/sealant material held in the microreservoir until dispensing is less than about 15 microliters.

37. The microapplicator of claim 36, wherein the small amount of the adhesive/sealant material held in the microreservoir until dispensing is less than about 10 microliters.

38. The microapplicator of claim 37, wherein the small amount of the adhesive/sealant material held in the microreservoir until dispensing is less than about 5 microliters.

39. The microapplicator of claim 1, wherein the applicator tip has a width of about 1 mm.

40. The microapplicator of claim 1, wherein the applicator tip is arranged to apply about 3 microliters or less.

41. The microapplicator of claim 1, wherein the applicator tip comprises a polymerization initiator or accelerator for the adhesive/sealant material.

42. The microapplicator of claim 1, wherein polymerization initiator or accelerator for the adhesive/sealant material is coated on an inside surface of the applicator tip.

43. A method of applying an adhesive or sealant material, comprising:

providing a microapplicator according to claim 1;

supplying a small amount, about 20 microliters or less, of an adhesive/sealant material to the microreservoir; and applying the adhesive/sealant to a substrate to be bonded.

44. The method of claim 43, wherein applying the adhesive/sealant comprises applying about 3 microliters or less of the adhesive/sealant material.

45. The method of claim 43, wherein the substrate to be bonded is biological tissue.

46. The method of claim 45, wherein the tissue comprises an incision or laceration.

47. The method of claim 43, wherein applying the adhesive/sealant comprises anastomosis.

48. The method of claim 43, wherein applying the adhesive/sealant comprises vascular anastomosis.

49. The method of claim 43, wherein applying the adhesive/sealant comprises duct anastomosis.

50. The method of claim 43, wherein applying the adhesive/sealant comprises at least one of reconstructing and reattaching biological tissue.

51. The method of claim 50, wherein the tissue comprises at least one of lymphatic, nerve and middle ear tissue.

52. The method of claim 43, wherein supplying the small amount of the adhesive/sealant material comprises moving a plunger toward the applicator tip.

53. The method of claim 43, wherein supplying the small amount of the adhesive/sealant material comprises breaking a frangible ampoule containing the adhesive/sealant material.

54. The method of claim 43, wherein supplying the small amount of the adhesive/sealant material comprises squeezing the handle portion.

55. The method of claim 43, wherein supplying the small amount of the adhesive/sealant material comprises dipping the applicator tip into a secondary reservoir of the adhesive/sealant material.

56. A delivery system for an adhesive or sealant material, the delivery system comprising:

a microapplicator having an applicator tip and a microreservoir at the applicator tip arranged to hold a small amount, about 20 microliters or less, of the adhesive/sealant material until dispensing; and a second reservoir containing the adhesive/sealant material, the second reservoir being connectable to the microapplicator to supply the adhesive/sealant material to the microreservoir at the applicator tip.

57. A method of applying an adhesive or sealant material, comprising:

providing a delivery system according to claim 56;

connecting the second reservoir to the microapplicator;

supplying a small amount, about 20 microliters or less, of the adhesive/sealant material to the microreservoir; and applying the adhesive/sealant to a substrate to be bonded.

58. The method of claim 57, wherein the substrate to be bonded is biological tissue.

59. The method of claim 58, wherein the tissue comprises an incision or laceration.

60. The method of claim 57, wherein applying the adhesive/sealant comprises anastomosis.

61. The method of claim 57, wherein applying the adhesive/sealant comprises vascular anastomosis.

62. The method of claim 57, wherein applying the adhesive/sealant comprises duct anastomosis.

63. The method of claim 57, wherein applying the adhesive/sealant comprises at least one of reconstructing and reattaching biological tissue.

64. The method of claim 63, wherein the tissue comprises at least one of lymphatic, nerve and middle ear tissue.

65. The method of claim 57, wherein supplying the small amount of the adhesive/sealant material comprises moving a plunger toward the applicator tip.

66. The method of claim 57, wherein supplying the small amount of the adhesive/sealant material comprises moving a plunger away from the applicator tip.

67. The method of claim 57, wherein supplying the small amount of the adhesive/sealant material comprises squeezing the second reservoir.

68. The method of claim 57, wherein supplying the small amount of the adhesive/sealant material comprises dipping the applicator tip in the second reservoir containing the adhesive/sealant material.

* * * * *

UNITED STATES PATENT AND TRADEMARK OFFICE
CERTIFICATE OF CORRECTION

PATENT NO.     : 6,547,467 B2
DATED          : April 15, 2003
INVENTOR(S)    : Julian A. Quintero It is certified that error appears in the above-identified patent and that said Letters Patent is hereby corrected as shown below:

Title page,
Item [56], References Cited, please insert the following

U.S. PATENT DOCUMENTS
| | | | |
|---|---|---|---|
| 2,721,858 A | 10/1955 | Joyner et al. | 260/67 |
| 3,254,111 A | 5/1966 | Hawkins et al. | 260/465.4 |
| 3,559,652 A | 2/1971 | Banitt et al. | 128/334 |
| 3,842,660 A * | 10/1974 | Van Buskirk | 73/61.54 |
| 3,940,362 A | 2/1976 | Overhults | 260/42.16 |
| 3,995,641 A | 12/1976 | Kronenthal et al. | 128/335 |
| 4,004,718 | 1/1977 | Wesley | 222/386 |
| 4,313,865 A | 2/1982 | Teramoto et al. | 260/31.4 |
| 4,364,876 A | 12/1982 | Kimura et al. | 260/465.4 |
| 4,560,723 A | 12/1985 | Millett et al. | 524/486 |
| 4,720,513 A | 1/1988 | Kameyama et al. | 523/203 |
| 5,130,369 A | 7/1992 | Hughes et al. | 524/846 |
| 5,163,929 | 11/1992 | Py | 604/298 |
| 5,216,096 A | 6/1993 | Hattori et al. | 526/201 |
| 5,328,687 A | 7/1994 | Leung et al. | 424/78.35 |
| 5,514,371 A | 5/1996 | Leung et al. | 424/78.35 |
| 5,514,372 A | 5/1996 | Leung et al. | 424/78.35 |
| 5,575,997 A | 11/1996 | Leung et al. | 424/78.35 |
| 5,582,834 A | 12/1996 | Leung e t al. | 424/426 |
| 5,624,669 A | 4/1997 | Leung et al. | 424/78.35 |
| 5,888,005 A * | 3/1999 | Gueret | 401/130 X |
| 5,928,611 A | 7/1999 | Leung | 422/131 |
| 5,944,702 | 8/1999 | Py | 604/298 |
| 5,976,102 | 11/1999 | Epstein | 604/35 |
| 5,989,205 A | 11/1999 | Pond et al. | 604/3 |
| 6,143,352 A | 11/2000 | Clark et al. | 4272.1 |
| 6,143,805 A | 11/2000 | Hickey et al. | 522/152 |
| 6,156,711 A * | 12/2000 | Perlman | 510/118 |
| 6,159,189 | 12/2000 | Finnemore et al. | 604/294 |
| 6,183,593 B1 | 2/2001 | Narang et al. | |
| 6,217,603 B1 | 4/2001 | Clark et al. | 606/214 |
| 6,238,120 B1 * | 5/2001 | Mark | 401/183 X |
| 6,238,212 B1 * | 5/2001 | Khachatoorian et al. | 433/89 |
| 6,310,166 B1 * | 10/2001 | Hickey et al. | |
| 6,328,715 B1 * | 12/2001 | Dragan et al. | 604/232 |

UNITED STATES PATENT AND TRADEMARK OFFICE
CERTIFICATE OF CORRECTION

PATENT NO. : 6,547,467 B2
DATED : April 15, 2003
INVENTOR(S) : Julian A. Quintero It is certified that error appears in the above-identified patent and that said Letters Patent is hereby corrected as shown below:

<u>Title page cont'd,</u>

FOREIGN PATENT DOCUMENTS

GB  2 107 328  A        4/1983
DE  3 701 250  A1       7/1988
WO  00/26284            5/2000
WO  00/69506           11/2000
WO  01/39669  A1        6/2001

OTHER PUBLICATIONS

U.S. patent application Ser. No. 09/630,437, Jonn et al., filed Aug. 2000.
U.S. patent application Ser. No. 09/919,877, Jonn et al., filed Aug. 2001.
U.S. patent application Ser. No. 09/430,289, D'Alessio et al., filed Oct. 1999.
U.S. patent application Ser. No. 09/430,177, Narang et al., filed Oct. 1999.
U.S. patent application Ser. No. 09/099,457, Malofsky et al., filed Jun. 1998.
U.S. patent application Ser. No. 09/430,180, Nicholson et al., filed Oct. 1999.
U.S. patent application Ser. No. 09/069,979, Narang et al., filed Apr. 1998.
U.S. patent application Ser. No. 09/430,176, Narang et al., filed Oct. 1999.

\* cited by examiner

Signed and Sealed this

Fourth Day of November, 2003

JAMES E. ROGAN
*Director of the United States Patent and Trademark Office*